(12) United States Patent
Eder

(10) Patent No.: US 11,944,555 B2
(45) Date of Patent: Apr. 2, 2024

(54) GRIPPING DEVICE

(71) Applicant: Otto Bock Healthcare Products GmbH, Vienna (AT)

(72) Inventor: Florian Eder, Vienna (AT)

(73) Assignee: OTTO BOCK HEALTHCARE PRODUCTS GMBH, Vienna (AT)

(*) Notice: Subject to any disclaimer, the term of this patent is extended or adjusted under 35 U.S.C. 154(b) by 53 days.

(21) Appl. No.: 15/733,337

(22) PCT Filed: Dec. 18, 2018

(86) PCT No.: PCT/EP2018/085659
§ 371 (c)(1),
(2) Date: Jul. 1, 2020

(87) PCT Pub. No.: WO2019/134826
PCT Pub. Date: Jul. 11, 2019

(65) Prior Publication Data
US 2021/0113353 A1   Apr. 22, 2021

(30) Foreign Application Priority Data

Jan. 5, 2018  (DE) .......................... 102018100173.8

(51) Int. Cl.
*A61F 2/50* (2006.01)
*A61F 2/58* (2006.01)
*A61F 2/70* (2006.01)

(52) U.S. Cl.
CPC .............. *A61F 2/586* (2013.01); *A61F 2/583* (2013.01); *A61F 2002/5038* (2013.01); *A61F 2002/5096* (2013.01); *A61F 2/70* (2013.01)

(58) Field of Classification Search
CPC ...................................................... A61F 2/586
See application file for complete search history.

(56) References Cited

U.S. PATENT DOCUMENTS

| 39,578 | A | * | 8/1863 | Kimball | ................ | A61F 2/586 |
| | | | | | | 623/57 |
| 1,324,564 | A | * | 12/1919 | Pringle | ................ | A61F 2/583 |
| | | | | | | 623/64 |
| 1,507,681 | A | | 9/1924 | Pecorella et al. | | |
| 2,549,074 | A | * | 4/1951 | Fishbein | ................ | A61F 2/583 |
| | | | | | | 623/64 |

(Continued)

FOREIGN PATENT DOCUMENTS

DE   450871   10/1927
DE   86242    12/1970

(Continued)

OTHER PUBLICATIONS

International Search Report for International Application No. PCT/EP2018/085659 dated Dec. 18, 2018, 5 pages.

*Primary Examiner* — Jacqueline Woznicki
(74) *Attorney, Agent, or Firm* — HOLLAND & HART LLP

(57) ABSTRACT

A gripping device having a chassis, at least one first finger element pivotally mounted on the chassis, at least one drive, and a force transmission element coupling the drive to the first finger element. The force transmission element pivots the first finger element relative to the chassis about two differently oriented pivot axes.

13 Claims, 11 Drawing Sheets

(56) References Cited

U.S. PATENT DOCUMENTS

| | | | |
|---|---|---|---|
| 2,553,827 A * | 5/1951 | Mason | A61F 2/583 |
| | | | 623/64 |
| 3,026,534 A * | 3/1962 | Brown | A61F 2/583 |
| | | | 623/64 |
| 3,694,021 A | 9/1972 | Mullen | |
| 2003/0163206 A1 * | 8/2003 | Yasui | B25J 17/0266 |
| | | | 623/24 |
| 2004/0195638 A1 | 10/2004 | Fischer et al. | |
| 2007/0213842 A1 * | 9/2007 | Simmons | A61F 2/68 |
| | | | 623/64 |
| 2008/0319553 A1 | 12/2008 | Puchhammer | |
| 2009/0016851 A1 | 1/2009 | Matsuda et al. | |
| 2012/0146352 A1 * | 6/2012 | Haslinger | A61F 2/586 |
| | | | 294/198 |
| 2012/0186383 A1 * | 7/2012 | Schvalb | B25J 9/104 |
| | | | 901/21 |
| 2014/0067083 A1 * | 3/2014 | Wenstrand | A61F 2/583 |
| | | | 623/24 |
| 2014/0114439 A1 * | 4/2014 | Iversen | A61F 2/586 |
| | | | 623/64 |
| 2015/0151433 A1 * | 6/2015 | Rust | B25J 15/0213 |
| | | | 294/106 |
| 2015/0230941 A1 * | 8/2015 | Jury | A61F 2/583 |
| | | | 623/64 |
| 2015/0351935 A1 * | 12/2015 | Donati | A61F 2/586 |
| | | | 623/24 |
| 2020/0206950 A1 * | 7/2020 | Fukaya | B25J 15/0226 |
| 2021/0113353 A1 * | 4/2021 | Eder | A61F 2/68 |

FOREIGN PATENT DOCUMENTS

| | | |
|---|---|---|
| DE | 102014007743 A1 | 12/2015 |
| EP | 1971297 B1 | 3/2012 |
| JP | S55-162758 | 5/1982 |
| JP | 2009519797 A | 5/2009 |
| WO | 2003017880 A1 | 3/2003 |
| WO | 2007076763 A2 | 7/2007 |

* cited by examiner

GRIPPING DEVICE

CROSS REFERENCE TO RELATED APPLICATIONS

This application is a U.S. National Entry and claims priority to PCT International Patent Application No. PCT/EP2018/085659, filed 18 Dec. 2018, and entitled "GRIPPING DEVICE", which claims priority to Germany Patent Application No. 10 2018 100 173.8 filed 5 Jan. 2018, the entire disclosures of which are incorporated herein by this reference.

TECHNICAL FIELD

The invention relates to a gripping device having a chassis, at least one first finger element mounted pivotably on the chassis, at least one drive, and a force transmission element coupling the drive to the first finger element. The gripping device is configured in particular as an orthopedic gripping device and is suitable for use as a prosthetic hand or as part of a prosthetic hand.

BACKGROUND

The purpose of a gripping device is to grip objects and to hold them securely in the gripped position. Different objects require different gripping devices in order to be able to be gripped optimally. The simplest gripping device is composed of two rod-like gripping elements which are displaceable relative to each other about a rigid pivot axis and are moved toward each other or away from each other. Flat objects, for example, can be easily gripped using such a gripping device. Problems arise when a gripping device is intended to be able to grip a large number of objects or is intended to be able to grip a large number of objects of different shapes. Such a problem arises in particular when the gripping device is used as an orthopedic gripping device in a hand prosthesis, since a patient or a user of a hand prosthesis is confronted on a daily basis with a large number of different objects that need to be gripped and held. In addition, in the case of a hand prosthesis, there is a need to simulate not just the function but also the appearance of a hand. For this purpose, finger elements are mounted on a chassis.

US 2004/00195638 A1 discloses a two-finger gripper in which two gripping devices can be moved from an opened position to a closed position in which the gripping devices lie directly opposite each other. An object located between the gripping devices can thus be held. To release the grip, a reversal of the direction of rotation of the drive can be initiated.

WO 03/017880 A1 relates to a prosthetic hand in which each individual prosthetic finger, which is mounted on a chassis, has a separate drive. The drive is arranged in the respective prosthetic finger. With such a prosthetic hand, it is possible to realize different gripping situations, for example a pinch grip or a lateral grip. Disadvantages here are the high degree of control needed for each individual finger, the complex technology with drives integrated in the fingers, and an increased susceptibility to faults due to the complex design.

DE 405 871 B1 describes an artificial hand with a chassis or palm on which rotatable fingers and a rotatable thumb are arranged. In the palm, a drive disk rotatable about an axis perpendicular to the flat of the hand is attached by connections to the fingers and thumb in such a way that rotation of the disk in one direction causes the fingers to open and rotation in the opposite direction causes the fingers to close. The rotation of the disk in one direction is effected by a cord; the return movement in the opposite direction is effected by a spring in the interior of the disk. Arranged on the circumference of the drive disk are locking teeth which are brought into engagement with a pawl and which hold the drive disk in the position that it has reached in its rotation by the cord.

EP 1 971 297 B1 describes a hand prosthesis comprising a chassis on which a plurality of prosthetic fingers are articulated or elastically mounted which, by means of a drive, are movable toward each other about at least one pivot axis relative to the chassis. Force transmission devices on a common drive are coupled to the prosthetic fingers via a coupling element in such a way that, proceeding from a rest position, and depending on the direction of rotation of the drive, at least two prosthetic fingers travel through different angles of adjustment in the same direction relative to the chassis, wherein the force transmission devices are coupled to the coupling element in such a way that their drive-side bearings have different dead center positions.

SUMMARY

The problem addressed by the present invention is to make available a gripping device in which different gripping positions can be reached in a simplified manner and with the least possible effort.

The invention, solves this problem by a gripping device having the features disclosed herein. Advantageous embodiments and developments of the invention are disclosed in the description and the figures.

The gripping device has a chassis, at least one first finger element mounted pivotably on the chassis, at least one drive, and a force transmission element coupling the drive to the first finger element, provision being made that the force transmission element pivots the first finger element relative to the chassis about two differently oriented pivot axes. By virtue of the finger element being mounted about two differently oriented pivot axes and by virtue of the first finger element being pivoted by the force transmission element about the two pivot axes, it is possible, through only one force transmission device, to move the first finger element to a different position via the drive and to be able to secure this position to a large extent. By virtue of the force transmission element being arranged at different coupling points on the first finger element, it is possible to achieve different orientations and positions through a combination of the different rotational movements about the two pivot axes, which results in an improved adaptability to the particular purpose of use and in an increased range of variation.

In addition to the one drive that pivots the finger element relative to the chassis about two differently oriented pivot axes, it is possible to provide further drives, which can be arranged in the finger element. For example, one phalanx can receive a drive or consist of a drive, which then serves as an auxiliary drive or as a positioning aid for adjusting the position of the phalanx.

The pivot axes about which the first finger element can be pivoted can be oriented perpendicularly with respect to each other, by which a simplified configuration of the movement of the finger can be achieved in accordance with the drive. If the two axes intersect each other, the movement of one axis cannot influence the movement of the other axis. In the case of axes that do not intersect each other, the rotation about the one axis can be utilized to initiate another movement.

The first finger element can be mounted pivotably on a support about one of the pivot axes, wherein the support is mounted pivotably on the chassis about the other pivot axis. The support thus constitutes a first connection between the chassis and the finger element that ultimately comes into contact with the object that is to be gripped. The support element permits the almost free positioning of the one pivot axis, by virtue of the possibility of designing the support in almost any desired way and of freely selecting the site and the orientation of the one pivot axis. The other pivot axis serves for securing the support on the chassis, so that this pivot axis is subject to some restriction as regards its arrangement. The support, as an intermediate piece between the chassis and the finger element, increases the design possibilities and the orientations of the pivot axes relative to each other.

In a variant of the invention, provision is made that the force transmission element is secured on the first finger. The securing can entail a direct securing of the force transmission element to the finger element. Without further force transmission elements being interposed, it is possible to achieve a direct coupling between the drive and the finger element. The force transmission element is not coupled to the support but instead directly to the finger element, such that a pivot axis formed by the support on the chassis is not coincident with a securing point of the force transmission element on the first finger element. Particularly when the force transmission element is mounted pivotably on the first finger element, the pivot axis about which the force transmission element is mounted on the finger element is coincident with the pivot axis with which the support element is mounted on the chassis. In this way, the distances between the bearing point of the force transmission element on the first finger element and the pivot axis on the chassis can be changed, as a result of which the forces or moments that can be transmitted via the drive are able to change. Likewise, different travel ratios can be set, as a result of which the gripping device is adaptable to the particular purpose of use.

In a further embodiment, the force transmission element is mounted on the first finger element by a cardan joint, wherein a degree of freedom in rotation about one pivot axis is blocked, as a result of which the finger element is rotatable about one of the pivot axes. By blocking a degree of freedom in rotation, it is possible to apply a torque about one of the pivot axes of the finger element. In an embodiment of the gripping device with a finger element mounted on a support, the degree of freedom about the support pivot axis is preferably blocked. The movement of the first finger element about the pivot axis formed on the support, the so-called support pivot axis, is thus predefined and effected by the movement of the force transmission element.

In an alternative embodiment, provision is made that the force transmission element is connected to the first finger element by a ball-and-socket joint, wherein the movement of the first finger element, in the same way as in the cardan bearing, is also controlled or predefined by the force transmission element. The drive changes the angle setting of the force transmission element in the main plane of the drive movement, which runs substantially perpendicular to the rotation axis of the drive. The force transmission element is pivoted in the main plane and, through the change of the angle setting on account of the rotation movement, controls the movement of the finger element. The ball-and-socket joint permits a free pivoting of the first finger element.

The force transmission element can be mounted on a rotatable bearing pin driven by the drive. The bearing pin can rotate on a circular disk or else can be mounted on an arm driven by the drive. If the force transmission element, preferably configured as a rigid structural part, for example a frame, a support that transmits tensile forces and compressive forces, or another substantially rigid structure, is mounted pivotably about the bearing pin, the force transmission element at the bearing point executes a circular movement or a movement in the shape of a segment of a circle or moves on a circular trajectory or on a trajectory in the shape of a segment of a circle. This movement preferably takes place in one plane, wherein the horizontal and vertical movement components of a circular movement in one plane serve to achieve a combined shift of the finger element about the two pivot axes.

The force transmission element can be mounted pivotably about an axis perpendicular to the longitudinal extent of the bearing pin, resulting in a cardan bearing or approximate cardan bearing of the force transmission element at the bearing point on the bearing pin. In this way, blockages in the movement can be prevented.

If the bearing pin is arranged on an arm, the latter can be mounted at a frame on a bearing arm pivotable about an axis, resulting in a superpositioning of rotational movements, which has the effect that the orientation of the force transmission element can be changed in different ways, as a result of which the pivoting of the finger element about the two pivot axes can be coordinated with each other.

The arm can be driven on a rotary disk mounted in the chassis, as a result of which the drive can be easily implemented by rotational movements.

The frame, on which the bearing arm is mounted and on which the arm and the bearing pin are thus also mounted, can be mounted displaceably in one plane on the chassis. By the displacement of the frame in one plane, further finger elements coupled to the first finger element can be driven. The displaceability can be influenced by a slotted guide, such that complex shifting movements of the frame and thus also individual movements of the further finger elements relative to the chassis are possible.

A pivot axis of the first finger element can intersect the axis formed by the bearing pin, such that a rotation about this axis does not influence the orientation of the first finger element with respect to this one pivot axis.

The embodiment of the force transmission element configured to transmit tensile force and to transmit compressive force permits precise control of the movement of the first finger element in all directions, such that a direct coupling between the drive and the finger element is possible without spring elements. In principle, it is possible to provide elastic components in the force transmission chain. The main purpose of these is not to reset the finger element to its starting position but to protect the mechanisms or to achieve a resilient movement behavior of the finger element under the effect of external forces, which is convenient for the user, especially in the case of orthopedic gripping devices. When the first finger element strikes an object, the interpositioning of elastic buffer elements can reduce a direct introduction of force into the drive, the motor, and, if appropriate, the bearing on a forearm stump.

In a development of the invention, provision is made that at least one second finger element is mounted pivotably on the chassis and is coupled to the drive in such a way that, proceeding from a rest position, and depending on the direction of rotation of the drive, the first and second finger elements travel on different trajectories relative to each other. By virtue of the different trajectories depending on the direction of rotation of the drive, it is possible to adopt different gripping positions, for example a lateral grip and a pinch grip, wherein the first finger element is rotatable about several pivot axes without having to provide a further drive. Simply through the choice of the direction of rotation of the drive, it is possible, with a single switching movement, for example by electromyographic impulses, to choose the respectively required grip or assign the finger elements in relation to one another.

The at least one second finger element can be coupled to the drive via a bracket mounted on the chassis so as to be foldable about an axis. The bracket permits almost any desired arrangement of a force transmission device, with which the bracket can be connected to the drive. In this way, settings can be adopted particularly easily, such that pivoting angles and force transmission ratios can be varied by different positioning of the first force transmission device between the drive and the bracket. The first force transmission device, which connects the drive to the bracket, can be mounted on an eccentrically moved bearing element that is coupled to the drive, such that, when the drive is actuated, the bracket, together with the first finger element, can be pivotably moved or folded in one direction or the other about the axis.

The bracket can be coupled to the at least one second finger element via a second force transmission device. The second force transmission device can be securable to the bracket at different sites such that, depending on the positioning of the second force transmission device on the bracket, different adjustment angles relative to the chassis can be achieved with the same angle of pivoting of the bracket relative to the chassis. In this way, the movements of the second finger elements relative to one another and of the second finger elements relative to the first finger element can be changed and adapted to the particular gripping situation or the particular purpose of use. The first force transmission device and also the second force transmission device can be configured to transmit tensile force and to transmit compressive force. In this way, resetting elements are not needed, and instead a constrained movement is achieved by changing directions of rotation of the drive.

In a development of the invention, provision is made that the bracket is designed to be elastically deformable, which results in the finger elements being resilient with respect to external forces, i.e. forces that are transmitted from the finger element to the chassis. By virtue of the elastic deformability, it is likewise possible to generate changes in the adjustment angle and in the respective trajectory.

As an alternative to driving the second finger elements via the bracket, it is possible to use the frame as a coupling element for the second force transmission device, such that, by way of the second force transmission device, the shifting of the frame relative to the chassis is transmitted to the second finger element coupled respectively via the second force transmission device.

BRIEF DESCRIPTION OF THE DRAWINGS

Illustrative embodiments of the invention are explained in more detail below with reference to the accompanying figures, in which.

DETAILED DESCRIPTION

Figure 1:
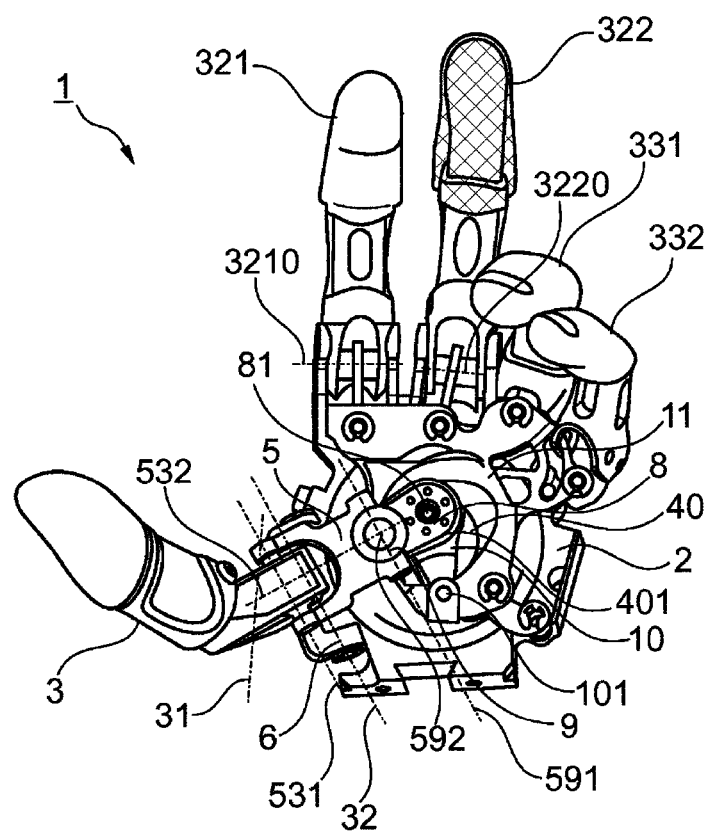
FIG. 1 shows a plan view of an opened gripping device in a first position.

FIG. 1 shows a bottom view of a gripping device 1 in the form of a prosthetic hand with a chassis 2 on which a dovetail recess is formed in order to mechanically connect the chassis 2 to proximal prosthesis components, for example a forearm shaft. A first finger element 3, configured as a thumb, is mounted pivotably on the chassis 2. Furthermore, four second finger elements 321, 322, 331, 332 are mounted pivotably on the chassis 2. The two second finger elements 321, 322 configured as index finger and middle finger are mounted on the chassis 2 via a respective pivot axis 3210, 3220; the second finger elements 331, 332 configured as ring finger and little finger are likewise mounted pivotably on the chassis 2 via a respective pivot axis 3310, 3320 (not visible). Furthermore, a motorized drive is secured on the chassis 2 and is arranged on the dorsal face or the side of the gripping device 1 corresponding to the back of the hand. By way of the drive, which will be explained later, a force transmission element 5 is driven which is in turn coupled to the first finger element 3, such that, upon a movement of the force transmission element 5, the finger element 3 is shifted relative to the chassis 2 and thus also relative to the other finger elements 321, 322, 331, 332. The chassis 2 forms a framework on which the finger elements are secured and in which the drive and the other components are mounted. The chassis substantially simulates the shape of a palm and has a main plane, which corresponds substantially to the palmar surface and, in the figure, is oriented parallel to the plane of the drawing.

The force transmission element 5 is configured as a rigid structural part and is H-shaped. On the drive side, the force transmission element 5 is mounted about two axes 591, 592 on a bearing pin 9, which constitutes an eccentric point of the rotary disk 40. The bearing arm 10 is secured pivotably about an axis 101 on a frame 11, which is mounted displaceably on the chassis 2. The bearing arm 10 is secured to the rotary disk 40 and is mounted pivotably about the axis 81. A further bearing pin, which forms a further eccentric point on the rotary disk 40, is formed about the axis 80. The frame 11 and also the rotary disk 40, the bearing arm 10 and the arm 8 are arranged substantially parallel to one another and parallel to the main plane of the chassis 2. The axis 101 of the pivot arm 10 runs parallel to the pivot axis 81 of the arm 8 and parallel to the axis 592 which is formed by the longitudinal extent of the pin 9 and about which the force transmission element 5 is rotatably mounted. The bearing of the force transmission element 5 is effected via a sleeve on which pins are arranged that form a second axis 591 oriented substantially orthogonally to the axis 592 formed by the longitudinal extent of the bearing pin 9. The two axes 591, 592 intersect each other. The second axis 591 runs substantially parallel to the plane in which the arm 8, the bearing arm 10 or the rotary disk 40 are arranged.

The end of the force transmission element 5 lying opposite the drive side is mounted pivotably on the first finger element 3 about a first axis 531, which is oriented substantially parallel to the second axis 591 on the bearing pin 9. The first finger element 3 is mounted on the chassis 2 via a support 6. The support 6 is mounted on the chassis 2 pivotably about a pivot axis 32 and, at the end directed away from the chassis 2, forms a second pivot axis 31, which is oriented differently than the chassis-side pivot axis 32. The first finger element 3 can thus be moved relative to the chassis 2 about two pivot axes 31, 32 that are formed by the support 6. The chassis-side pivot axis 32 is oriented such that the first finger element 3 can be pivoted outward or extended, such that the first finger element 3 is pivoted in the direction of a plane in which the frame 11 or the rotary disk 40 is located. In an embodiment of the gripping device as a prosthetic hand, this plane corresponds to the palmar surface. When pivoted in the other direction or flexed, the first finger element 3 moves about the chassis-side pivot axis 32 in the direction of the opposite second finger elements 331, 322, i.e. substantially perpendicularly with respect to the plane of the drawing according to FIG. 1.

In the illustrative embodiment shown, the finger-side pivot axis 31 does not intersect the chassis-side pivot axis 32 and runs in a plane that is oriented orthogonally with respect to the chassis-side pivot axis 32. It is thereby possible that the first finger element 3 can be pivoted about the finger-side pivot axis 31, wherein the pivoting movement can take place in the direction of the index finger 321 or away from the latter. To ensure that this is possible in the case of a rigid force transmission element 5, the force transmission element 5 is mounted on the finger element 3 so as to be pivotable not only about the first axis but also about a second axis 532, thus resulting in a cardan bearing that is blocked in a rotational degree of freedom, in order to transmit force to pivot the finger element about the finger-side pivot axis 31 when the force transmission element 5 is moved by the drive.

If the arm 8 is rotated counterclockwise about a rotation axis 401 of the rotary disk 40 and the bearing arm 10 is pivoted clockwise about the axis 101, the force transmission element 5 moves to the right. The axis 591 pivots clockwise about the bearing pin 9, and the first finger element 3 is moved about the chassis-side pivot axis 32 in the direction of the palmar surface or of the opposite second finger element 332, which, in the case of a prosthetic hand, corresponds to the little finger. A reverse movement and shifting of the axis 591 in the direction of the chassis-side pivot axis 32, i.e. to the left, would cause pivoting about the chassis-side pivot axis 32 and thus cause opening of the gripping device 1 or an outward movement of the first finger element 3. At the same time, on account of the change of orientation of the bearing pin 9 relative to the finger-side pivot axis 31, a pivoting movement of the finger element 3 about the finger-side pivot axis 31 is effected. Since the first finger element 3 does not run parallel to or coaxial to the finger-side pivot axis 31 but instead protrudes therefrom, i.e. the longitudinal extent of the first finger element does not coincide with the pivot axis 31, the orientation of the first finger element 3 relative to the chassis 2 thus also changes, and moreover the distance and angle with respect to the other second finger elements 321, 322, 331, 332. Proceeding from the position of maximum opening or extension, which is more or less reached in FIG. 1, different trajectories and movement patterns of the respective finger elements 3, 321, 322, 331, 332 are obtained depending on the direction of rotation of the drive and the pivoting movement of the bearing pin 9 in conjunction with the pivoting of the arm 8 or of the bearing arm 10.

Figure 2:
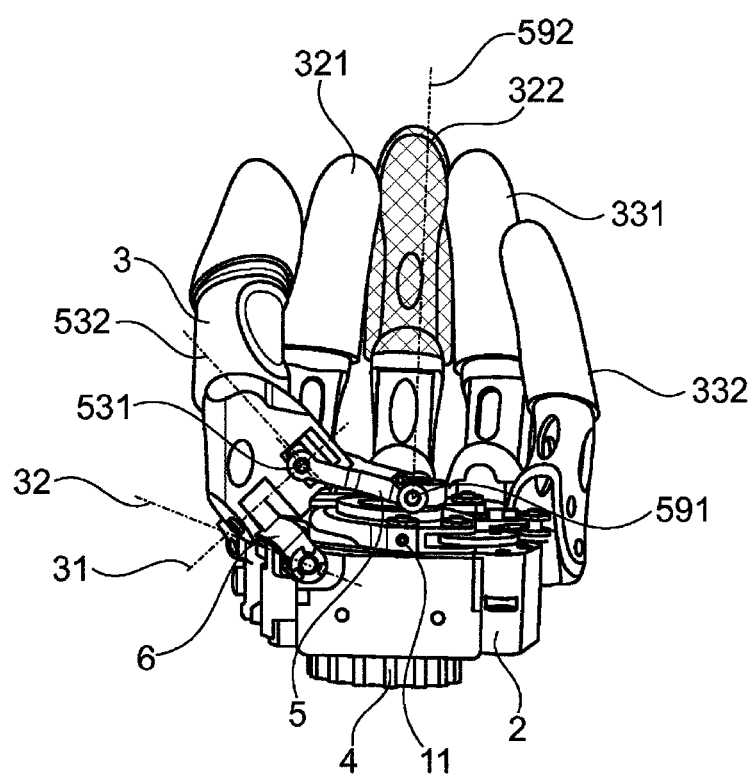
FIG. 2 shows a side view of the gripping device in the lateral grip.

FIG. 2 shows a side view from the direction of the proximal attachment point, i.e. in the region of the dovetail guide for securing the gripping device 1 to a further component, for example a forearm shaft. The drive 4, in the form of an electric motor, can be seen on the side of the chassis 2 directed away from the force transmission element 5. By way of the drive 4, and possibly with interposition of a gear, the rotary disk 40 and thus the bearing arm 10 and arm 8 and the frame 11 are moved inside the chassis 2. FIG. 2 shows the arrangement, in parallel planes, of the frame 11 with the rotary disk 8 and the bearing arm 10 and arranged above this the arm 8. The axis 591 runs substantially parallel to the plane of the frame 11, whereas the second axis 592 is oriented perpendicularly with respect to this plane and corresponds to the longitudinal extent of the bearing pin 9. The chassis-side pivot axis 32 likewise runs substantially parallel to the plane of the frame 11, such that the support 6, with its two pivot axes 32, 31 oriented perpendicular to each other and at a distance from each other, can be pivoted into a plane parallel to the plane of the frame 11 or perpendicularly thereto about the chassis-side pivot axis 32. The finger element 3 can additionally be pivoted about the finger-side pivot axis 31. FIG. 2 also shows the orientation of the first axis 531 which, in this illustrative embodiment, extends parallel to the axis 591 through the two pins perpendicular to the bearing pin 9. To generate a cardan bearing, the axis 531 is cardanically mounted via a bearing body that is pivotable about the second axis 532. FIG. 2 shows the position of the gripping device in what is called a lateral grip, in which the first finger element 3 is placed laterally against the nearest second finger element 321, as is needed for example to grip flat elements such as paper or the like. Such a position of the finger elements 3, 321 is reached when the drive 4 is moved such that, proceeding from the opened and extended position according to FIG. 1, the second finger elements 321, 322 are pivoted upward, from the plane or main plane formed by the frame 11, more quickly than the first finger element 3, which is additionally pivoted forward, i.e. about the finger-side pivot axis 31.

Figure 3:
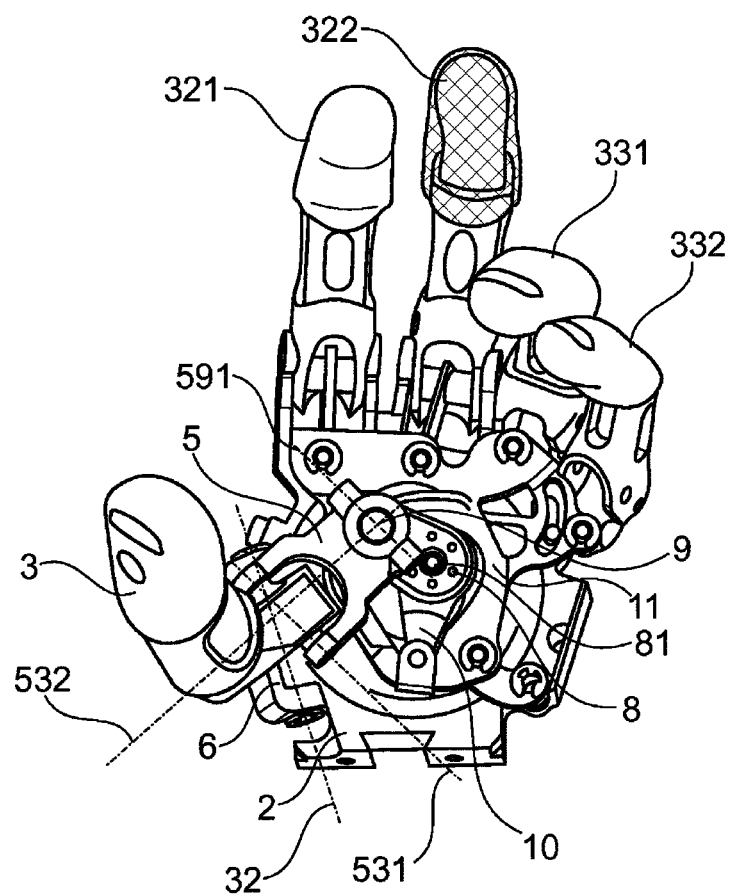
FIG. 3 shows a view according to FIG. 1 in a partially closed position.

FIG. 3 shows a position of the finger elements 3, 321, 322, 331, 332 in which the bearing pin 9 has been pivoted clockwise proceeding from the starting position according to FIG. 1. The rotation axis 81 of the arm 8 has likewise been moved clockwise about the rotation axis 401 of the rotary disk 40. The bearing arm 10 is moved downward by the movement of the rotation axis 81. In this way, the frame 11 is also pivoted clockwise and thus moved downward by the bearing about the axis 101. In this way, the second finger elements 321, 322, 331, 332 are pivoted about their respective pivot axes, such that the gripping device is increasingly closed, when the finger elements 3, 321, 322, 331, 332 are flexed. The first finger element 3 has been rotated counterclockwise about the finger-side pivot axis 31, while at the same time a pivoting has taken place about the chassis-side pivot axis 32 in the direction of the other second finger elements 321, 322, 331, 332, such that the axis 531 has been rotated counterclockwise and, in a further movement of the bearing pin 9, the first finger element 3 is brought together with the two second finger elements 331, 332. This further movement and the united position is shown in FIG. 4.

The frame 11 is moved further downward and the bearing arm 10 is rotated further clockwise about the axis 101, likewise the arm 8, such that the bearing pin 9 is moved further to the right along a movement path. The distal ends of the finger elements 3, 321 touch; a further movement of the bearing pin 9 would lead to an increased pressing force of the finger elements 3, 321 on each other. The position shown in FIG. 4 is what is called the pinch grip, in which the tips of the curved finger elements 3, 321, 322 bear on each other.

Figure 4:
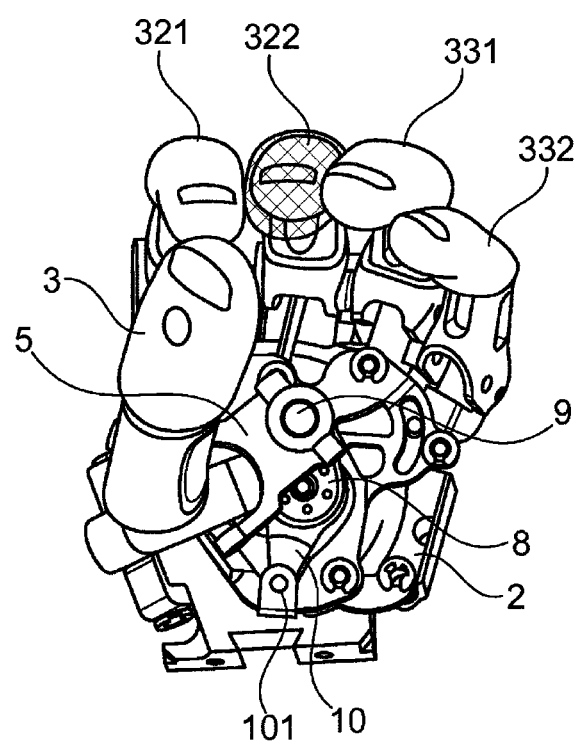
FIG. 4 shows a view according to FIG. 3, in a closed position in the pinch grip.
Figure 5:
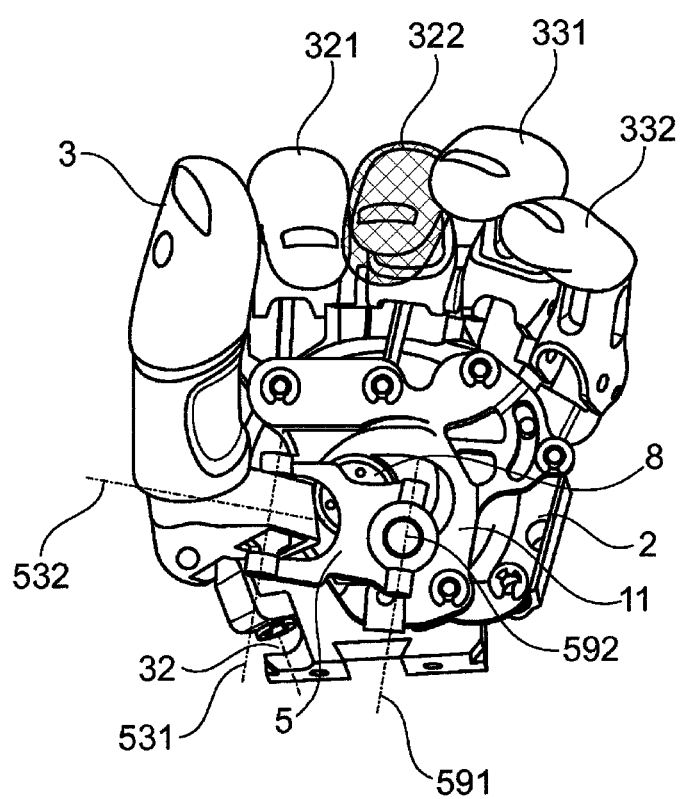
FIG. 5 shows a bottom view of the position according to FIG. 2.

FIG. 5, by contrast, shows the alternative end position, in which the bearing pin 9 is rotated to the maximum extent counterclockwise. The so-called lateral grip brings the first finger element 3 laterally onto the second finger element 321; the frame 11 is moved further downward, compared to FIG. 4, such that the second finger elements 321, 322, 331, 332 are pivoted further out of the main plane of the chassis 2 to a closed position before contact with the first finger element 3 is reached.

Figure 6:
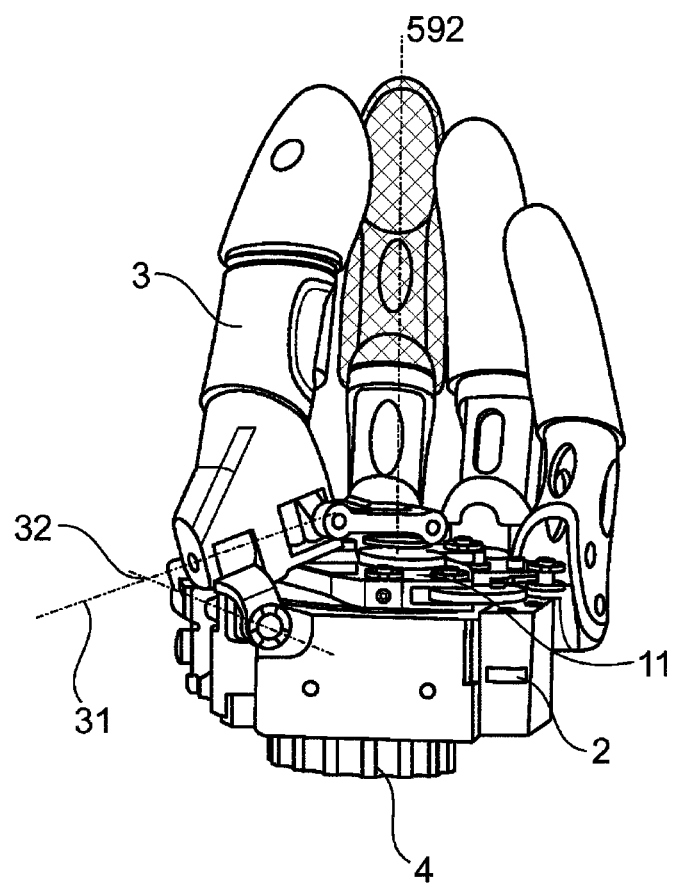
FIG. 6 shows a side view of the position according to FIG. 4.

The pinch grip according to FIG. 4 is shown in a side view in FIG. 6; all of the finger elements 3, 321, 322, 331, 332 have been pivoted upward to the maximum extent from the plane of the frame 11 or the main surface or palmar surface to a flexed position.

Figure 7:
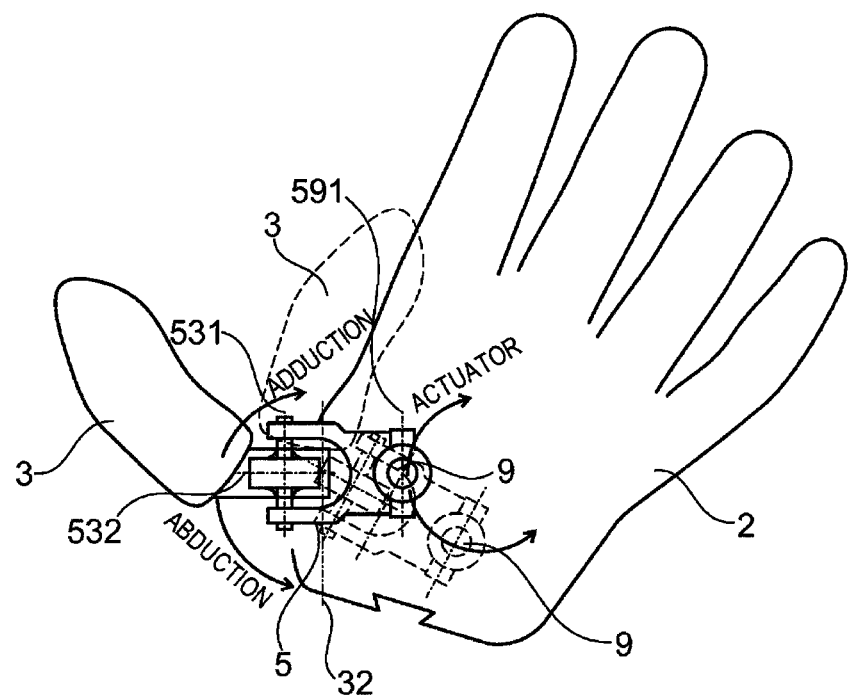
FIG. 7 shows a schematic bottom view of the gripping device.

FIG. 7 shows a schematic view of the gripping device in the position according to FIG. 1, indicated by solid lines, and in the position according to FIG. 5, indicated by broken lines. The bearing, the drive and the arrangement of the second finger elements are not shown here. Proceeding from the position of maximum opening of the gripping device, the force transmission element 5 is pivoted counterclockwise along a circular path, such that the bearing pin 9 migrates upward and toward the right on the circular path. By the movement portion toward the right, the first finger element 3 pivots about the chassis-side pivot axis 32 and performs a closing movement; the downward movement portion causes the pivoting about the finger-side pivot axis 31, resulting in an adduction of the first finger element 3, i.e. the latter is drawn toward the chassis 2 and the second finger elements. The end position, indicated here by the broken lines, corresponds to the position of the lateral grip shown in FIG. 5. Upon pivoting by the drive 4 in the opposite direction, i.e. in the clockwise direction, the bearing pin 9 is moved upward and toward the right, as a result of which, in addition to the closing movement about the chassis-side pivot axis 32, there is an abduction movement about the finger-side pivot axis 31, such that the pinch grip is obtained in the respective end position, as is shown in FIG. 4.

Figure 8:
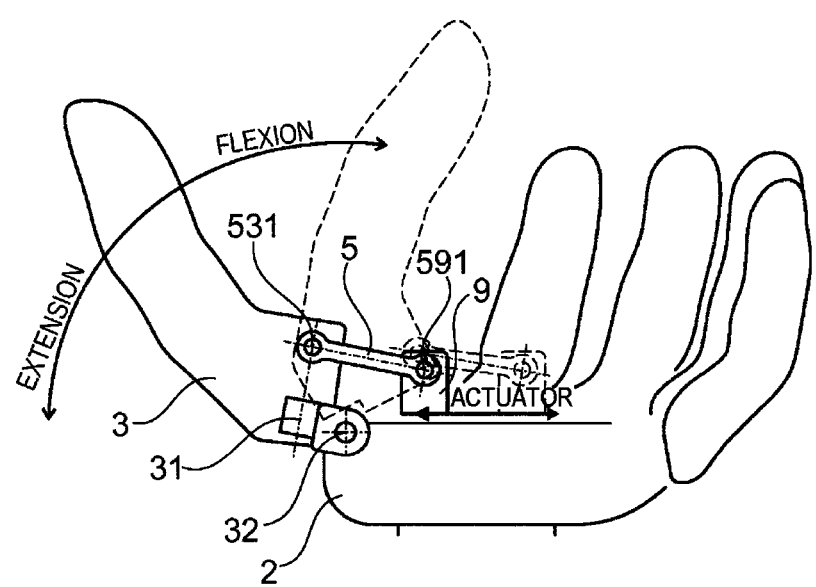
FIG. 8 shows a schematic side view according to FIG. 7.

FIG. 8 is a side view showing the movement of the first finger element 3 relative to the chassis 2. In a pivoting movement proceeding from the starting position according to FIG. 7, a flexion of the first finger element 3 relative to the chassis 2 is effected by the movement component away from the chassis-side pivot axis 32, whereas, in an opposite movement, an extension is effected, i.e. an enlargement of the angle between the first finger element 3 on the part of the force transmission element 5 relative to the chassis 2. The flexed position is indicated by broken lines, the extended position by solid lines. The finger-side first axis 531 of the force transmission element 5 lies above the second axis 591 about which the force transmission element 5 is mounted pivotably on the bearing pin 9. By means of a displacement of the axis 591 in the main plane, a displacement of the axis 531 and thus a pivoting of the support 6 and of the finger element 3 arranged thereon is possible about the chassis-side pivot axis 32.

Figure 9:
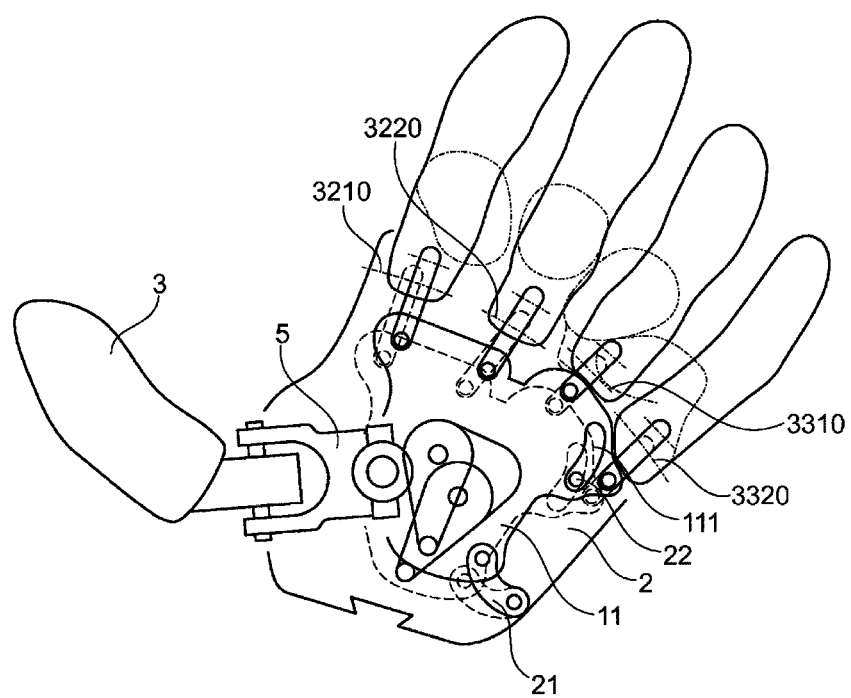
FIG. 9 shows a bottom view of a variant of the drive of the second finger elements.

FIG. 9 shows, in a schematic view, the movement of the second finger elements 321, 322, 331, 332 through the shifting of the frame 11 relative to the chassis 2. By means of the drive, the frame 11 is moved in a curved slotted guide 111, in which a pin 22 of the chassis is guided. Furthermore, a pivot arm 21 is mounted on the chassis 2 and is mounted pivotably with the frame 11 in the region of the fastening point of the gripping device. If, proceeding from the starting position indicated by solid lines, the frame 11 is shifted downward by the drive 4, the frame 11 moves along the slotted guide 111 and around the pivot arm 21 to the position indicated by broken lines. The second finger elements 321, 322, 331, 332 pivot about the respective pivot axes 3210, 3220, 3310, 3320, since the frame 11 is coupled to the second finger elements 321, 322, 331, 332 via second force transmission elements 51.

Figure 10:
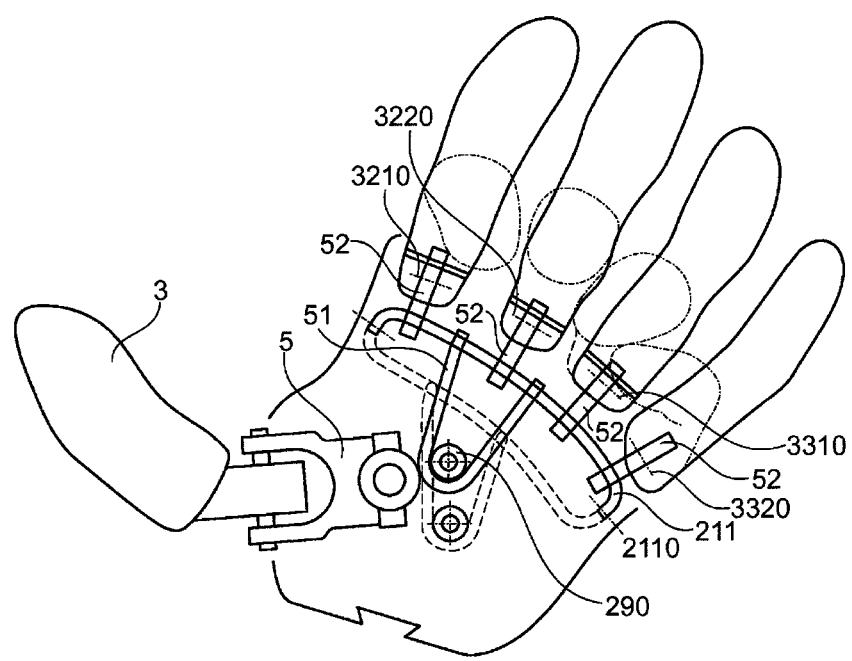
FIG. 10 shows a plan view of a variant of the drive of the second finger elements.

An alternative way of driving the second finger elements is shown in FIG. 10. Instead of a frame 11, a bracket 211 is mounted on the chassis 2 pivotably about a pivot axis 2110. The bracket 211 can be shifted from the illustrated extended position of the second finger elements 321, 322, 331, 332 to a flexed position about the axis 2110. The second finger elements 321, 322, 331, 332 are then located in a closed position, and the bracket 211 is pivoted away from the pivot axes 3210, 3220, 3310, 3320, as is indicated by the broken lines. In order to execute this pivoting movement of the bracket 211, the bracket 211 is connected to the drive 4 via a first force transmission device 51. The first force transmission device 51 is mounted on an eccentrically mounted bearing element 290 or pin that is coupled to the drive 4. In the illustrative embodiment shown, the force transmission device 51 is configured as a loop which is placed around the bearing element 290. The first force transmission device 51 can slide along the bearing element 290 such that, in the circular movement executed by the bearing element 290 upon a rotation from a position in maximum proximity to the axis 2110 to a position at a maximum distance from the axis 2110, a length compensation takes place between the two portions of the force transmission device. The force transmission device 51 can be mounted pivotably and, if appropriate, displaceably on the bracket 211. The bracket 211 can be made of an elastic material, for example an elastic synthetic material.

Figure 11:
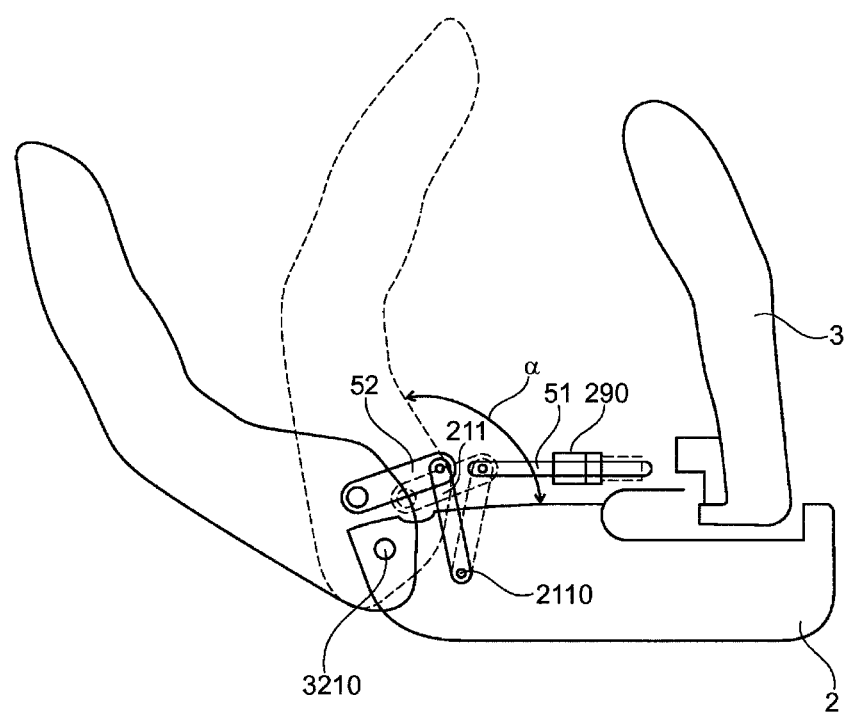
FIG. 11 shows a side view of FIG. 10.

FIG. 11 shows, in a side view, the actuation of the second finger elements by means of the bracket 211. In the starting position, the second finger elements are extended, that is to say the angle α between the main plane of the chassis 2 and the side of the second finger element directed toward the force transmission device 51 is at a maximum. The enclosed angle α is at a minimum in the view indicated by broken lines, that is to say the second finger elements are almost perpendicular to the main plane of the chassis 2. The bearing element 290 is at a maximum distance from the axis 2110 of the bracket 211 such that, by the shifting of the bearing element 290 and the pivoting of the bracket 211 and the associated pivoting of the second force transmission device coupling the bracket 211 to the respective second finger elements, the respective second finger element pivots about the respective pivot axis on the chassis.

I claim:

1. A gripping device comprising:
   a chassis;
   at least one first finger element mounted pivotably on the chassis;
   a single drive;
   a force transmission element coupling the single drive to the at least one first finger element, wherein the force transmission element pivots the at least one first finger element relative to the chassis about two differently oriented pivot axes, wherein at least one second finger element is mounted pivotably on the chassis and is coupled to the single drive in such a way that, proceeding from a rest position, and depending on a direction of rotation of the single drive, the first and second finger elements travel on different trajectories relative to each other, and wherein the force transmission element is rigid and configured to transmit tensile force and compressive force.

2. The gripping device as claimed in claim 1, wherein the pivot axes are at least one of oriented perpendicularly with respect to each other and do not intersect each other.

3. The gripping device as claimed in claim 1, wherein the at least one first finger element is mounted on a support pivotably about one of the pivot axes, and the support is mounted pivotably on the chassis about the other pivot axis.

4. The gripping device as claimed in claim 3, wherein the force transmission element is secured on the at least one first finger element.

5. The gripping device as claimed in claim 4, wherein the force transmission element is mounted pivotably on the at least one first finger element.

6. The gripping device as claimed in claim 5, wherein the force transmission element is mounted on the at least one first finger element by a cardan joint or by a ball-and-socket joint, and movement of the at least one first finger element about one of the pivot axes is controlled by the force transmission element.

7. The gripping device as claimed in claim 1, wherein the force transmission element is mounted pivotably about a bearing pin on a rotatable arm driven by the single drive.

8. The gripping device as claimed in claim 7, wherein the force transmission element is mounted pivotably about an axis oriented perpendicular to a longitudinal extent of the bearing pin.

9. The gripping device as claimed in claim 7, wherein the rotatable arm is mounted at a frame on a bearing arm pivotable about an axis.

10. The gripping device as claimed in claim 9, wherein the frame is mounted displaceably in one plane on the chassis.

11. The gripping device as claimed in claim 7, wherein the rotatable arm is driven by a rotary disk mounted in the chassis.

12. The gripping device as claimed in claim 7, wherein one pivot axis of the two differently oriented pivot axes of the at least one first finger element intersects an axis formed by the bearing pin.

13. The orthopedic gripping device as claimed in claim 1, wherein a frame is coupled to the second finger element.

* * * * *